United States Patent [19]
Holsclaw

[11] Patent Number: 4,877,400
[45] Date of Patent: Oct. 31, 1989

[54] DENTAL BRIDGE AND METHOD

[76] Inventor: Linda A. Holsclaw, 2420 Forest Meadow, Lewisville, Tex. 75067

[21] Appl. No.: 210,802

[22] Filed: Jun. 24, 1988

[51] Int. Cl.[4] .............................................. A61C 13/22
[52] U.S. Cl. .................................... 433/183; 433/213; 433/218
[58] Field of Search ............... 433/180, 181, 182, 219, 433/213

[56] References Cited

U.S. PATENT DOCUMENTS 4,445,862  1/1984  Chiaramonte et al. ............. 433/181
4,713,005  12/1987  Marshall et al. ..................... 433/180

*Primary Examiner*—Robert Peshock
*Attorney, Agent, or Firm*—Macdonald J. Wiggins

[57] ABSTRACT

An improved dental bridge and method of construction thereof is disclosed. The bridge has no exposed metal. The abutment teeth are prepared and have opposing notches cut into the occlusal surfaces thereof. Impressions are made and a master and opposing model prepared therefrom. The model abutment teeth are prepared as dies and a refractory model then developed from the master model. A metal pontic rod is prepared, opaqued, and installed in the refractory model notches. After coating the abutment teeth and pontic rod with a porcelain mix and curing, all porcelain crowns are built over the abutment models and one or more all porcelain pontics are built over the pontic rod. After curing and glazing of the dental bridge, the refractory model is cut away from the bridge.

12 Claims, 2 Drawing Sheets

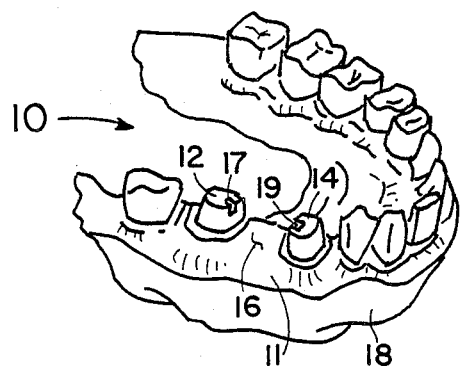
FIG. 1
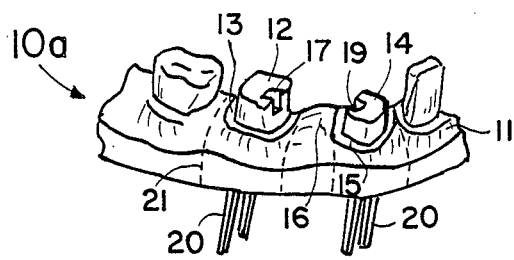
FIG. 2
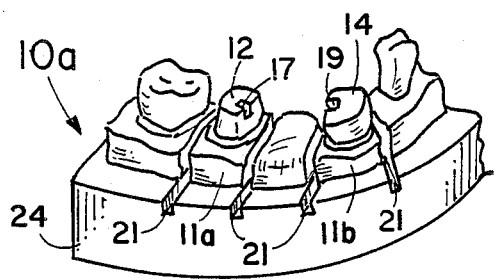
FIG. 3
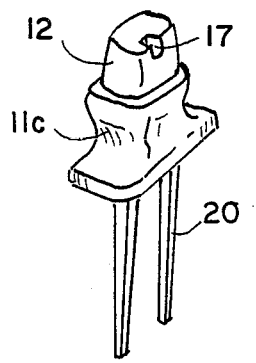
FIG. 4
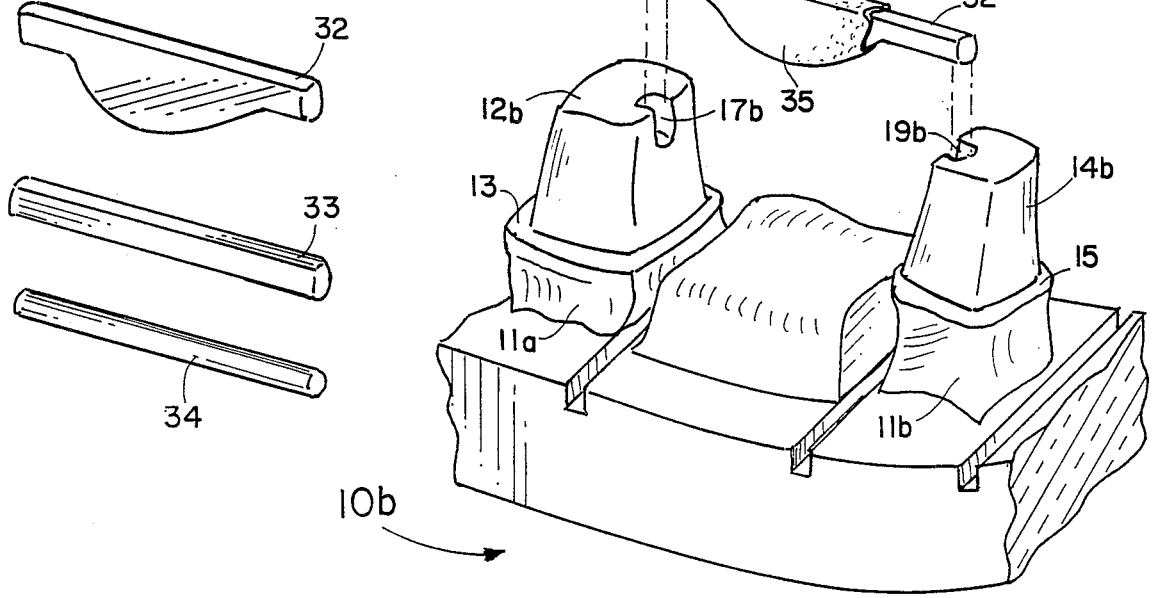
FIG. 5
FIG. 6

DENTAL BRIDGE AND METHOD

BACKGROUND OF THE INVENTION

1. Field of the Invention

The present invention relates to fixed dental bridges, and more particularly to a bridge having no exposed metal and method of making same.

2. Description of the Prior Art

Fixed dental bridges are utilized to replace one or more lost natural teeth when the lost teeth are between sound natural teeth. In the prior art, each of the patient's abutment teeth are ground to provide a shoulder, and an impression is made. The dental laboratory prepares a model from the impression and prepares a cast metal framework to fit over the abutment teeth of the model. The framework also includes the form of the replacement tooth or teeth. Next, the framework is finished to accept an opaquing treatment. Thereafter, the framework is coated with porcelain to form crowns over the abutment teeth and the pontic. The porcelain is then ground and glazed.

Generally, the metal is exposed along the margins of each crown or tooth and is polished. Internal metal surfaces of the bridge are sandblasted to permit cementing to the patient's prepared abutment teeth. As will be recognized, exposed metal is cosmetically undesirable, and some patients experience gum resorption or allergic reactions when a non-precious metal is used.

Thus, there is a need for a bridge construction in which no exposed metal is present and which presents a more natural appearance.

SUMMARY OF THE INVENTION

The present invention is a dental bridge and the method of construction thereof. The bridge of the invention provides an all-porcelain appearance which can closely match the appearance of the patient's natural teeth. The invention utilizes a pontic rod preferably having an essentially rectangular cross section. The rod is thinly coated with opaque porcelain and baked. When the patient's abutment teeth are prepared conventionally, a notch to match the cross sectional shape of the ends of the pontic rod is cut in the distal portion of the occlusal surface of the mesial abutment and in the mesial occlusal surface of the distal abutment.

In the laboratory, a master model is made from the impression prepared by the dentist. As is known in the art, the prepared abutment teeth are sawed out to form removable dies to permit trimming of the gum area of the model to expose the margin. The dies are painted with a die spacer and replaced in the master model. An impression is then made from the master model.

A refractory model is then made by pouring refractory investment material into the master model impression and firing. As will be recognized, a refractory model of the original patient's impression is now available. The bridge area of the refractory model is treated with a porcelain slurry to seal the refractory material to inhibit excretion of gases from the model. At this point in the process, the pontic rod is prepared to fit between the abutment teeth and to properly seat in the prepared notches. The metal pontic rod is opaqued and installed in the notches of the abutment teeth. A coating of porcelain mix is applied to the abutment teeth of the refractory model. The refractory model is then baked to the temperature required for the type of porcelain being used.

As will now be understood, the development of a refractory model from the master model permits the pontic rod to be attached to the model abutment teeth, a coating of porcelain applied, and the porcelain coating baked at high temperatures without damage to the model. Next, the bridge is built on the refractory model using standard body and incisal porcelain for the abutment teeth crowns and the pontic. When building of the crowns and pontic is complete, the model is again baked at the temperature required by the porcelain.

The final steps of grinding the bridge teeth into proper occlusal contact and overall contour is carried out. The bridge is then glazed and baked. The bridge is removed from the refractory model by cutting away the model with a cutoff disc and by use of low pressure sandblasting with glass beads or a suitable abrasive.

The bridge is then ready for installation by the dentist. As will be noted, the use of metal is limited to the pontic rod which is completely covered. Thus, no metal is visible and the bridge will not be easily distinguishable from the patient's natural teeth.

It is therefore a principal object of the invention to provide a dental bridge and method of preparing in which no metal will be visible when installed.

It is another object of the invention to provide a dental bridge and method of preparing having a metal pontic bar for supporting a porcelain pontic and all-porcelain abutment teeth crowns.

It is still another object of the invention to provide a method of preparing a dental bridge which permits abutment teeth thereof to be x-rayed.

It is yet another object of the invention to provide stock pontic rods for implementing a bridge having all-porcelain crowns.

These and other objects and advantages of the invention will become apparent from the following detailed description when read in conjunction with the drawings.

BRIEF DESCRIPTION OF THE DRAWINGS

FIG. 1 is a perspective view of an exemplary master model of a patient's prepared teeth;

FIG. 2 is a perspective view of the relevant portions of the master model of FIG. 1 for a base;

FIG. 3 is a perspective view of the master model portions of FIG. 2 on the base and having die teeth cut to permit removal;

FIG. 4 shows a die removed from the model of FIG. 3 and undercut;

FIG. 5 is a perspective view of three designs of pontic rods;

FIG. 6 shows a coated pontic rod with the coating partially cut away indicating installation in the abutment teeth;

DETAILED DESCRIPTION OF THE PREFERRED EMBODIMENT

Figure 7:
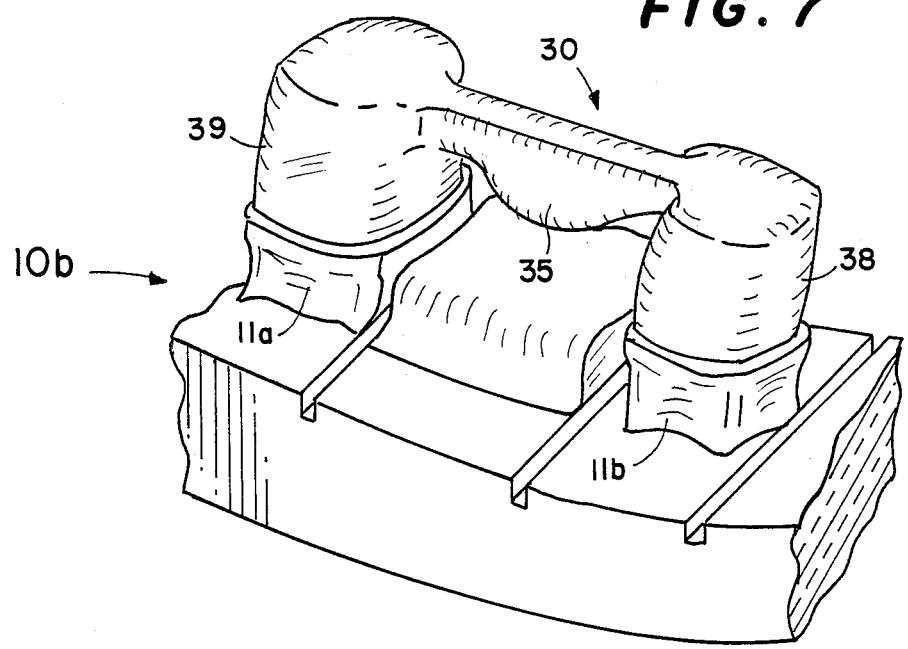
FIG. 7 is a perspective view of the pontic rod and abutment teeth with an initial coating of porcelain.

The method of the invention will be described with reference to a dental bridge which comprises a pontic for replacing a single tooth and a pair of crowns for the abutment teeth. The first step in the method is preparation of the abutment teeth by reducing each tooth by at least 3 mm and maintaining approximately the original tooth shape and providing a shoulder or champfer margin around each abutment tooth. As will be described in detail hereinafter, a spoon or cup shaped notch is formed in the distal portion of the occlusal surface of the mesial abutment and an opposing notch in the mesial portion of the occlusal surface of the distal abutment.

Next, an upper and lower impression of the patient's mouth is taken. The impressions are poured, preferably in dental die stone, to produce a model. The impression containing the prepared teeth is referred to as the master impression and the model made therefrom is the master model. The other impression and model produced therefrom are referred to as the opposing impression and model.

Turning now to FIG. 1, a poured master model 10 of the prepared teeth is shown. Model tooth 12 is the distal abutment having notch 17 formed therein. Model tooth 14 is the mesial abutment having notch 19 aligned with and opposing notch 17. Space 16 represents the space of a missing tooth which is to be replaced by the bridge. Surface 11 represents the gum area of the master model. Portion 18 is overflow from pouring of the master model.

The next step is to prepare master model 10 for a base by removing portion 18 therefrom. FIG. 2 shows the relevant portion of master model 10. In accordance with the invention, it is required to remove model teeth 12 and 14 from the master model, to undercut the gum area 16 to expose the margins 13 and 15, and to thereafter replace the model teeth 12 and 14 in the master model. To this end, metal pins 20 have been inserted into model teeth 12 and 14 in FIG. 2. The trimmed underside of master model 10 is painted with a separation material to permit the model teeth 12 and 14 to be separated from the base. The dotted lines 21 indicate the desired removable areas.

A base 24 is prepared and the trimmed master model 10a is mounted thereon as shown in FIG. 3. Saw cuts 21 are made through master model 10a to permit model teeth 12 and 14 to be removed from base 24. Model teeth 12 and 14 are referred to at this point as "dies" for forming crowns for the patient's prepared teeth. The surfaces of dies 12 and 14 are painted with a die spacing material to compensate for space which will be required by cement when the crowns to be prepared are seated on the patient's prepared teeth.

In the next step, the dies 12 and 14 are removed from the model and the areas representing the gum tissue is trimmed away to expose the margin areas 13 of the dies. FIG. 4 shows die 12 removed from the master model 10a and the trimmed gum tissue area 11c. The completed crowns will extend to the margin area 13.

Next, the invention utilizes a refractory model method for making crowns that will fit the prepared teeth. As will be understood, the refractory model 10b is required to be an exact duplicate of the trimmed master model 10a. To form the refractory model 10b, an impression is made of the master model 10a, with the trimmed and painted dies in place, using vinyl polysiloxane impression material. The impression is poured up using a refractory investment material. Next, the refractory model is dried for 20 minutes at 1200° F. After drying, the refractory model 10b is fired under vacuum. Preferably, firing begins at 1200° F. and the temperature is increased at a rate of 90° F. per minute to 1950° F. The refractory model 10b is thereafter cooled very slowly.

The dies 12b and 14b are next coated with a slurry mix of porcelain to seal the surfaces for inhibiting gases from entering the next layer of porcelain. The next step is to prepare a pontic rod. FIG. 5 shows three pontic rod designs 32, 33, and 34. Rod 32 is a truss type, rod 33 is an essentially rectangular bar, and rod 34 is a cylindrical shape. However, other shapes may be suitable. The following description will use truss type pontic rod 32 for exemplary purposes. The material of rod 32 must be a metal to which porcelain may be applied. Examples are: nickel-chrome; chrome cobalt; Ag-PD; and Au-PD. The mesial and distal ends of rod 32 must overlap the occlusal surface of the mesial and distal abutments a distance of at least 0.5 mm. Preferably, the ends of rod 32 are flat and formed to fit in the notches of the occlusal surfaces of the abutments.

After the pontic rod 32 is prepared to fit between notches 17b and 19b of the refractory model 10b, it is thinly coated with opaque porcelain 35 as shown in FIG. 6 to prevent the metal from being visible in the finished bridge. The coated rod 30 is then fired. In accordance with the invention, preformed pontic rods may be made available to the dental profession in a range of sizes, either coated, in metal form, or in wax form. The ends of opaqued pontic rod 30 are inserted in notches 17b and 19b and the abutment teeth 12b and 14b and pontic rod 30 of FIG. 6 are coated with a thicker mix of porcelain. The refractory model 10b is then baked at the recommended temperature for the type of porcelain used. Typically, 1800° F. is suitable. The bridge portion of the model will now appear as shown in FIG. 7.

Figure 8:
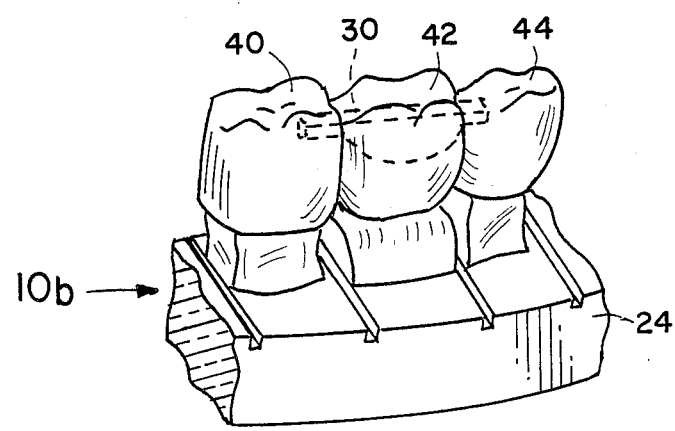
FIG. 8 is a perspective view of the completed bridge on the refractory model.

After baking and cooling, the crowns and pontic for the bridge are built using standard body and incisal porcelain over coatings 38, 39 and 35 of FIG. 7, and will appear as in FIG. 8. The body and incisal porcelain is baked. After cooling, the occlusal surfaces of the bridge are ground into proper occlusal contact and overall contour using the opposing master model. Glaze is then applied, dried and baked at the recommended temperature.

At this point, the bridge is ready to be removed from the refractory model 10b. The refractory material is carefully cut away from the bridge. As will be known to those of skill in the art, the major portions of the model may be removed using a cutoff disc. The material in the crown portions may then be removed by sandblasting using glass beads or aluminum oxide abrasive material. No more than 30 psi of air pressure should be used.

Figure 9:
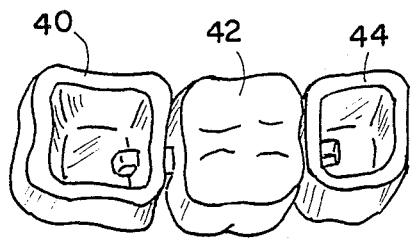
FIG. 9 is a bottom view of the bridge ready for installation on the patient's teeth.

FIG. 9 shows a bottom view of the exemplary bridge of the invention after removal from the refractory model 10b. The ends of the opaqued pontic rod 30 may be seen in the respective interiors 46, 48 of crowns 40, 44 which will seat in the notches in the patient's prepared teeth.

Although an exemplary embodiment of a bridge utilizing a single pontic in accordance with the invention has been disclosed, the strength of the metal pontic rod permits multiple pontics as well as posterior bridges to be constructed. The absence of metal in the crowns allows the dentist to monitor underlying vital abutments by use of standard x-ray techniques. The pontic rod metal is completely enclosed and any risk of patient reaction to the metal is thus eliminated.

Variations in the disclosed method and bridge construction are possible without departing from the spirit and scope of the invention.

I claim:

1. A method of constructing a dental bridge for a patient having a pair of reduced and prepared abutment teeth and a space therebetween, said preparation including forming a first notch in the distal portion of the occlusal surface of the mesial abutment tooth and a second notch in the mesial occlusal surface of the distal abutment tooth, and for which teeth an impression has been made, comprising the steps of:
   (a) forming a master model from said impression;
   (b) forming first and second dies of the modeled abutment teeth;
   (c) forming a refractory model from the master model;
   (d) making a pontic rod to fit in and between said first and second notches of said refractory model;
   (e) disposing said pontic rod in said first and second notches of the refractory model;
   (f) covering the refractory model abutment teeth and pontic rod with a mix of porcelain;
   (g) baking said refractory model to cure porcelain mix;
   (h) building a crown of porcelain over each of the refractory model abutment teeth, and at least one pontic of porcelain over the pontic rod to form the dental bridge;
   (i) baking the crowns and the pontic; and
   (j) removing the dental bridge from the refractory model.

2. The method as recited in claim 1 in which step (b) includes the steps of:
   inserting pins into the first and second dies;
   mounting the master model on a base having the pins inserted into the base;
   sawing the master model to permit removal and reinstallation of the first and second dies from the base; and
   undercutting a gum-representing area of the first and second dies.

3. The method as recited in claim 1 in which said step of forming a refractory model includes the steps of:
   making an impression of the master model;
   pouring up the master model impression using a refractory investment material; and
   firing the refractory model.

4. The method as recited in claim 3 in which the step of firing includes the steps of:
   drying the refractory model; and
   baking the dried refractory model in a vacuum.

5. The method as recited in claim 1 in which the step of making a pontic rod includes the steps of:
   coating the pontic rod with opaque porcelain; and
   baking the coated pontic rod.

6. The method as recited in claim 1 in which the step of removing the bridge from the refractory model includes the step of cutting away the refractory model.

7. The method as recited in claim 1 which further includes the step of:
   grinding the bridge into proper occlusal contact.

8. The method as recited in claim 1 which further includes the step of:
   applying a glaze to an exterior surface of the bridge.

9. A method of constructing a porcelain dental bridge having no visible metal portions for a patient having a reduced and prepared mesial abutment tooth and a reduced and prepared distal abutment tooth, said teeth having a tooth space therebetween, comprising the steps of:
   (a) forming a first notch in the distal portion of the occlusal surface of the mesial abutment tooth;
   (b) forming a second notch in the mesial portion of the occlusal surface of the distal abutment tooth;
   (c) making upper and lower impressions of the patient's teeth;
   (d) making a master model and an opposing model from the impression, the master model including modeled abutment teeth;
   (e) exposing margins of the modeled abutment teeth of the master model to form first and second dies;
   (f) making a refractory model from the master model;
   (g) making a metal pontic rod to fit in and between said first and second notches of the refractory model;
   (h) baking a coating of opaque porcelain over the pontic rod;
   (i) disposing the coated pontic rod in the first and second notches of the refractory model;
   (j) coating the refractory model abutment teeth and pontic rod with a porcelain mix;
   (k) curing the porcelain mix;
   (l) building a crown of porcelain over each of the refractory model abutment teeth;
   (m) building a porcelain pontic over the pontic rod;
   (n) curing the porcelain crowns and pontic to thereby form the dental bridge; and
   (o) cutting away the refractory model to remove the dental bridge therefrom.

10. A dental bridge for replacing at least one missing natural tooth in which reduced and prepared first and second abutment teeth include opposing first and second notches in the occlusal surfaces thereof comprising:
    a pontic rod having first and second ends formed to fit in and between said first and second notches of said abutment teeth;
    an opaque coating over said pontic rod;
    a first all porcelain crown formed to fit said reduced and prepared first abutment tooth, said first end of said pontic rod embedded in a portion of said first crown;
    a second all porcelain crown formed to fit said reduced and prepared second abutment tooth, said second end of said pontic rod embedded in a portion of said second crown; and
    at least one all porcelain pontic formed between said first and second crowns supported therebetween by said pontic rod.

11. The bridge as recited in claim 10 in which said pontic rod is formed of metal.

12. The bridge as recited in claim 10 in which said first and second porcelain crowns and said pontic are coated with a glaze.

* * * * *